(12) United States Patent
Leamon

(10) Patent No.: US 6,379,698 B1
(45) Date of Patent: Apr. 30, 2002

(54) FUSOGENIC LIPIDS AND VESICLES

(75) Inventor: Christopher Paul Leamon, West Lafayette, IN (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/287,175

(22) Filed: Apr. 6, 1999

(51) Int. Cl.$^7$ ................................................ A61K 9/127
(52) U.S. Cl. .................... 424/450; 435/320.1; 435/455; 435/458; 514/44
(58) Field of Search ................... 424/450; 435/320.1, 435/455, 458; 514/2, 44

(56) References Cited

U.S. PATENT DOCUMENTS

| | | | |
|---|---|---|---|
| 5,013,556 A | | 5/1991 | Woodle et al. ............... 424/450 |
| 5,100,662 A | * | 3/1992 | Bolcsak et al. ............... 424/88 |
| 5,264,618 A | * | 11/1993 | Felgner et al. ............... 560/224 |
| 5,395,619 A | | 3/1995 | Zalipsky et al. ............. 424/450 |
| 5,614,503 A | * | 3/1997 | Chaudhary et al. ........... 514/44 |
| 5,635,487 A | | 6/1997 | Wolff et al. .................... 514/44 |
| 5,635,784 A | * | 6/1997 | Wolff et al. .................... 514/44 |
| 5,688,488 A | * | 11/1997 | Low et al. ................... 424/1.69 |
| 5,747,471 A | * | 5/1998 | Siegel et al. ................... 514/44 |
| 6,169,078 B1 | * | 1/2000 | Hughes et al. ................. 514/44 |
| 6,303,302 B1 | * | 2/2000 | Legendre et al. .......... 424/1.96 |
| 6,043,094 A | * | 3/2000 | Martin et al. ................ 435/458 |
| 6,045,821 A | * | 4/2000 | Garrity et al. ............... 424/450 |
| 6,180,134 B1 | * | 1/2001 | Zalipsky et al. ............. 424/450 |
| 6,224,903 B1 | * | 5/2001 | Martin et al. ................ 424/450 |

FOREIGN PATENT DOCUMENTS

| | | | |
|---|---|---|---|
| WO | 90/07924 | * | 7/1990 |
| WO | 99/38821 | * | 8/1998 |

OTHER PUBLICATIONS

Chu, C. et al., "Efficiency of Cytoplasmic Delivery by pH–Sensitive Liposomes to Cells in Culture," *Pharmaceutical Research*, vol. 7, No. 8, (1990) p. 824–834.

Ropert, C., et all, "Oligonucleotides Encapsulated in pH Sensitive Liposomes are Efficient Toward Friend Retrovirus," *Biochemical and Biophysical Research Communications*, vol. 183, No. 2 (1992) p. 879–885.

Tang, F., et al., "Introduction of a Disulfide Bond into a Cataionic Lipid Enhances Transgene Expression of Plasmid DNA," *Biochemical and Biophysical Research Communications*, vol. 242, (1998) p. 141–145.

Wrobel, I., et al., "Fusion of Cationic Liposomes with Mammalian Cells Occurs After Endocytosis," *Biochemica et Biophysica Acta*, vol. 1235 (1995) p. 296–304.

\* cited by examiner

*Primary Examiner*—Dave T. Nguyen
(74) *Attorney, Agent, or Firm*—Woodcock Washburn LLP

(57) ABSTRACT

Novel lipid compounds are provided that may be termed "pro-cationic" in that they are neutral or negatively charged until they are either brought into contact with cellular membranes or are internalized by cells. The lipids have a hydrophobic tail group and a hydrophilic head group, the head group incorporating both a positively and negatively charged region at physiological pH. The hydrophobic tail group is stably connected to the positive region of the head group which in turn is connected to the negative region by a disulfide bond that is susceptible to cleavage by membrane-bound and intracellular factors. Cleavage of the disulfide bond removes the negatively charged region from the head group resulting in a lipid that is cationic and therefor fusogenic with negatively charged cell membranes. Consequently, lipids of the invention are useful as components of liposomes that serve as vehicles for delivering pharmaceutical agents into cells with reduced toxicity.

1 Claim, 3 Drawing Sheets

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
tcccgcctgt gacatgcatt                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
gcccaagctg gcatccgtca                                                   20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
gcgtttgctc ttcttcttgc g                                                 21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
gttctcgctg gtgagtttca                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
tccgtcatcg ctcctcaggg                                                   20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6

```
gcgtttgctc ttcttcttgc g                                              21

<210> SEQ ID NO 7
<211> LENGTH: 8
<212> TYPE: DNA
<213> ORGANISM: Artificial Sequence
<220> FEATURE:
<223> OTHER INFORMATION: Description of Artificial  Sequence:
      Oligonucleotide

<400> SEQUENCE: 7 ttggggtt                                                              8
```

FUSOGENIC LIPIDS AND VESICLES

FIELD OF THE INVENTION

The present invention is related to novel lipid compounds and vesicles as well as formulation and delivery of pharmaceutical agents using said lipids and vesicles.

BACKGROUND OF THE INVENTION

Liposomes are vesicles composed of a bilayer of lipid molecules, much like natural cellular membranes, and lo have been developed to deliver pharmaceutical agents.

Pharmaceutical agents, including those not normally taken up by cells because they are too large to pass through membrane channels, or are degraded in plasma may be delivered by encapsulating the agent within a liposome. It is believed that due to their structural similarity with membranes, liposomes and their contents are taken up by cells. Unfortunately, cellular uptake of liposomes is to a great extent by an endocytotic mechanism, resulting in the liposomes being engulfed in endosome or lysosome organelles only to be degraded and/or expelled as waste along with their pharmaceutical contents. Consequently, an often insufficient amount of the pharmaceutical agent ever becomes present in the cellular cytoplasm or nucleus where it is active.

In an attempt to address the problems associated with endocytosis, liposomes comprising cationic lipids, sometimes referred to as "fusogenic" liposomes, have been developed. These liposomes fuse with cellular and intracellular membranes due to electronic attraction between negatively charged phospholipids of membranes and the positively charged liposome (Wrobel et al, Biochimica et Biophysica Acta, 1995, 1235:296). Thus when fusion of liposome and membrane occur, the contents of the liposome is expelled across the membrane. An example of such a liposome is lipofectin which comprises the cationic lipid DOTMA (N-(1-(2,3-dioleoyloxy)propyl)-N,N,N-trimethylamine). Other cationic lipids having been formulated into liposomes include DOTAP (1,2-dioleoyloxy-3-(triethylammonium)-propane), DOGS (N,N-dioctacedylamidoglycylspermine) and DDAB (dimethyl-dioctadecyl-ammonium-bromide). However, a problem associated with cationic liposomes is that when administered in vivo, they tend to bind various factors such as proteins in the plasma resulting in the formation of aggregates that are too large to enter cells. Such aggregates are believed to circulate poorly in the vasculature and accumulate in lungs and possibly cause pulmonary embolisms.

It would therefore be desirable to provide lipids and liposomes that are fusogenic with membranes and thus capable of delivering pharmaceutical agents to tissues or cells yet do not have the inherent aggregation problems associated with cationic lipids and liposomes.

SUMMARY OF THE INVENTION

In accordance with an aspect of the present invention there are provided lipid compounds comprising a hydrophobic tail portion covalently linked to a hydrophilic head portion, wherein said hydrophilic head portion comprises:

a first region proximal to said hydrophobic tail portion having a net positive charge at physiological pH;

a second region distal to said hydrophobic tail portion having a net negative charge at physiological pH; and a disulfide bond connecting said first and second regions.

In another aspect of the invention there is provided liposomes comprising lipid compounds having a hydrophobic tail portion covalently linked to a hydrophilic head portion, wherein said hydrophilic head portion comprises:

a first region, proximal to said hydrophobic tail portion, having a net positive charge at physiological pH;

a second region, distal to said hydrophobic tail portion, having a net negative charge at physiological pH; and a disulfide bond connecting said first and second regions.

At physiological pH, liposomes of the invention are zwitterionic (charge balanced) or are negatively charged carrying both positive and negative charges. However, once in a cellular micro environment, reduction of the disulfide bond effects cleavage of the negative region leaving the remainder of the lipid and liposome with an overall cationic character which then readily associates with cellular and intracellular membranes.

In yet another aspect, there is provided a method of delivering a pharmaceutical agent to an animal, comprising administering a liposome composition of the invention to said animal.

DETAILED DESCRIPTION OF THE INVENTION

Figure 1:
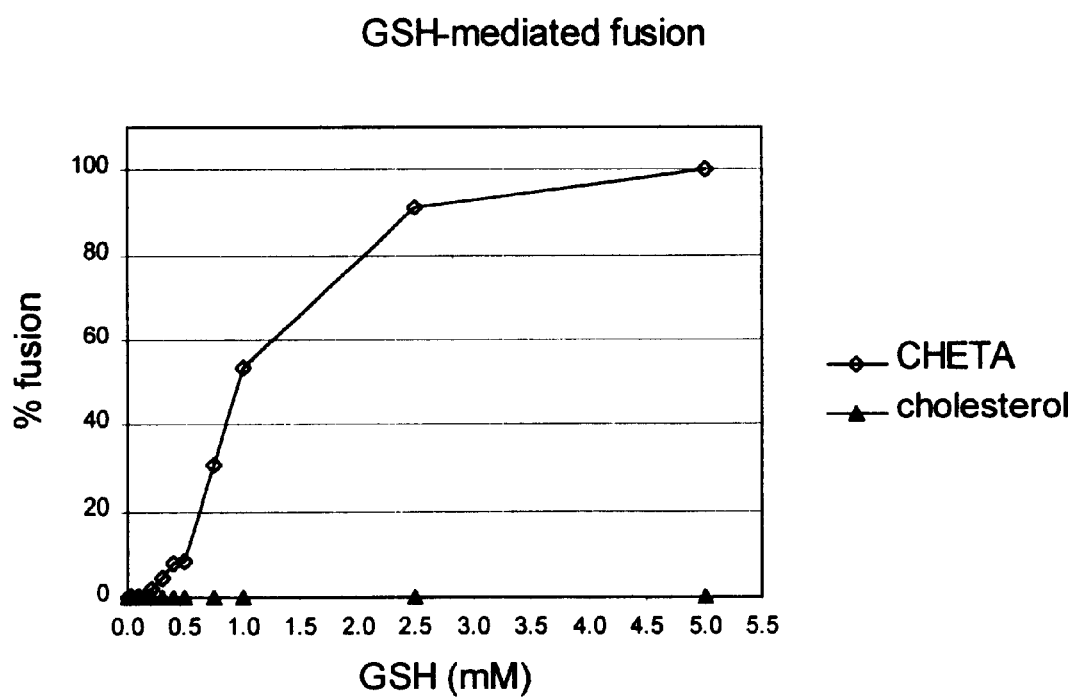
FIG. 1 is a graph illustrating fusion of negatively charged liposomes with procationic liposomes comprising CHETA lipids of the invention and control liposomes comprising cholesterol lipids treated with disulfide reducing agent glutathione (GSH).
Figure 2:
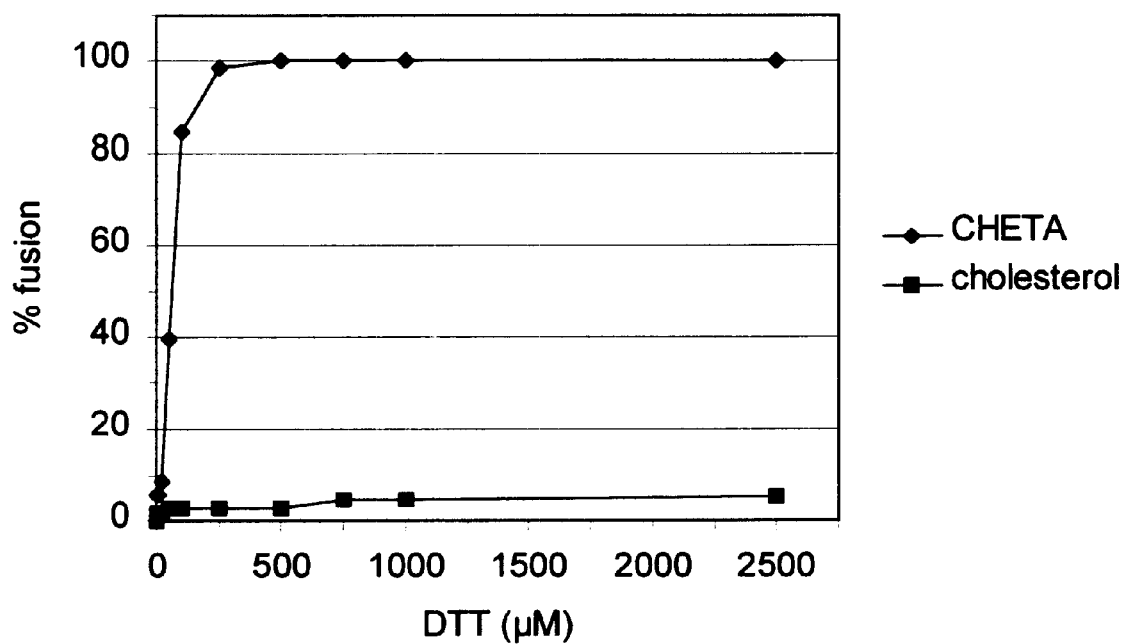
FIG. 2 is a graph illustrating fusion of negatively charged liposomes with procationic CHETA is liposomes and control cholesterol liposomes treated with reducing agent dithiothreitol (DTT).
Figure 3:
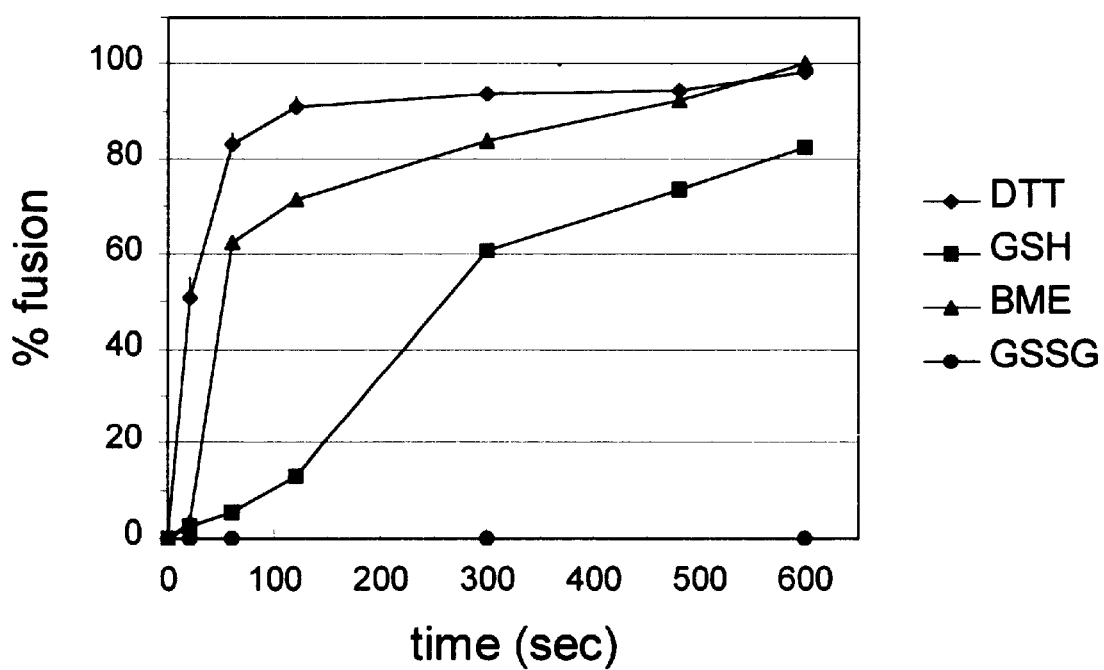
FIG. 3 is a graph illustrating the kinetics of liposome fusion with procationic CHETA liposome (CHETA) treated with disulfide reducing agents dithiothreitol (DTT), β-mercaptoacetic acid (BME), glutathione (GSH) and a control non-disulfide reducing oxidized glutathione dimer (GSSG).

In accordance with an aspect of the present invention there are provided lipid compounds that comprise a hydrophobic tail portion covalently linked to a hydrophilic head portion, wherein said hydrophilic head portion comprises a first region proximal to said hydrophobic tail portion having a net positive charge at physiological pH; a second region distal to said hydrophobic tail portion having a net negative charge at physiological pH; and a disulfide bond connecting said first and second regions. By "physiological pH" is meant a pH range of approximately 6.5 to 8.0, preferably about 7.0 to 7.6 and more preferably about 7.2 to 7.6. Most preferably physiological pH is about 7.4.

At physiological pH said lipid compounds of the invention are zwitterionic or are overall negatively charged having both positively and negatively charged regions within the same compound. The overall charge of the lipid compounds i.e. the sum of the charges may be positive, neutral or negative, but are preferably neutral or negative e.g. 0 to about −5. More preferably, lipid compounds of the invention have an overall charge of −1 or −2 and most preferably −1. In such preferred embodiments wherein the sum of the charges is 0 or negative, the lipid compounds may be called "pro-cationic" since they are initially neutral or negative yet become positively charged following in-situ disulfide bond reduction.

Upon administration to an animal, lipid compounds of the invention react with cellular or subcellular membrane components or intracellular factors which reduce and cleave disulfide bonds thereby removing the negatively charged region of the hydrophilic head portion. The resulting lipid compound without the negative region has an overall net positive charge which serves to bring the lipid or liposome into close proximity of cellular or intracellular membranes by way of electrostatic interaction. Lipids according to this particular embodiment are neutral or slightly negative yet become cationic in-situ or in the cellular or subcellular microenvironment.

The disulfide bond of the lipid compounds are reduced or cleaved by components of the cell membrane such as thioredoxin and protein disulfide isomerase. These proteins are also components of intracellular membranes, in particular endosome and lysosome membranes in which it is believed that much of the administered lipid/liposome accumulates as a result of endocytosis. Other factors which reduce or cleave the disulfide bond connecting the charged regions of the lipids include glutathione which is present in relatively high concentrations in cells while present extracellularly in concentrations too low to reduce disulfide bonds to an appreciable extent.

In a preferred embodiment, the hydrophobic tail portion of lipid compounds of the invention comprise one or two independent saturated or unsaturated aliphatic hydrocarbon chains of 3 to 30 carbon atoms in length. Preferred aliphatic hydrocarbon chains include lauryl (dodecanyl), myristyl (tetradecanyl), palmityl (hexadecanyl), stearyl (octadecanyl), oleyl (9(Z)-octadecenyl), elaidyl (9(E)-octadecenyl), linoleyl (9(Z),12(Z)-octadecadienyl), linolenyl (9(Z),12(Z),15(Z)-octadecatrienyl), eleostearyl (9(Z),11(E),13(E)-octadecatrienyl), phytanyl (3,7,11,15-tetramethylhexadecanyl) and alkoxy (-oxy), acyl (-oyl) or acyloxy (-oyloxy) équivalents thereof. Alternatively the tail portion may be a single steroidal moiety such as lanosterol or cholesterol which may be linked to the hydrophilic head portion via the 3-position oxygen.

In a particular embodiment, the hydrophilic head portion of lipid compounds of the invention is peptidic or partially peptidic. In a preferred embodiment the net positive region of the head portion (proximal to the hydrophobic tail) comprises one or more lysine (Lys, K) or arginine (Arg, R) amino acid residues which are positively charged at physiological pH. In another embodiment, the negatively charged region of the head portion (distal to the hydrophobic tail) may comprise one or more aspartate (Asp, D) or glutamate (Glu, E) amino acid residues which are negative at physiological pH. Further, the disulfide bond connecting the positive and negative regions of the hydrophilic head portion may be formed by one or two cysteine amino acid residues, one associated with the positive region and/or the other from the negative region.

Preferred lipid compounds of the invention may be represented by the general formula (I):

X—Y—S—S—Z (I)

wherein:

X is selected from

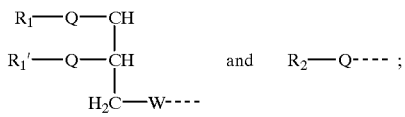   and   R$_2$—Q----  ;

R$_1$ and R$_1$' are independently selected from straight or branched C$_{3-30}$ alkyl, alkenyl and alkynyl;

Q is O, OC(O), C(O)O, HNC(O), C(O)NH, OC(O)NH, or C(O);

W is CHR$_3$, NR$_3$, —N$^+$(R$_3$)$_2$—, O, S, —C(O)NH—, —NH(CO)—, —OC(O)NH— or —O—P(O) (OR$_3$) —O—;

R$_2$ is the same as R$_1$ or is a steroid group;

R$_3$ is H or C$_{1-4}$ alkyl;

Y is C$_{1-12}$ alkylene, C$_{2-12}$ alkenylene or C$_{2-12}$ alkynylene optionally substituted with alkyl, amino, aminoalkyl, guanidino, guanidinoalkyl, amidino or amidinoalkyl, and optionally interrupted with —NR$_3$—, —N$^+$(R$_3$)$_2$—, —C(O)—, —NH—C(NH)—, —C(NH)NH— or —NH—C(NH)—NH—, or Y is an amino acid residue or a peptide; and Z is a C$_{1-12}$ alkyl, alkenyl, alkynyl optionally substituted with alkyl, carboxyl, carboxyalkyl, an amino acid residue, a peptide, oliognucleotide, or a targeting molecule attached via a linking group;

provided that at physiological pH, X and Y together have a net positive charge and Z has a net negative charge.

In a particular embodiment, X is the group

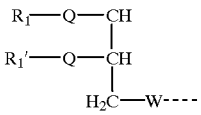

wherein R$_1$, R$_1$', Q and W are as previously defined. In preferred embodiments, R$_1$ and R$_1$' are independently selected from lauryl, myristyl, palmityl, stearyl, oleyl, elaidyl, linoleyl, linolenyl, eleostearyl and phytanyl. More preferably R$_1$ and R$_1$' are both oleyl, stearyl or phytanyl. In a particular embodiment Q is C(O)O. In another particular embodiment Q is O.

In a particular embodiment, W is a divalent group selected from —N$^+$ (R$_3$)$_2$—, O, —OC(O)NH— and —O—P(=O) (OR$_3$) —O— wherein R$_3$ is H or C$_{1-4}$ alkyl. In a particular embodiment W is —OC(O)NH—. In another embodiment W is the group —OP(O) (OR$_3$) –O— wherein R$_3$ is H and more preferably R$_3$ is C$_{2-4}$ alkyl e.g. methyl or ethyl such that the group is not negatively charged at physiological pH. In another embodiment, W is a positively charged group —N$^+$(R$_3$)$_2$— wherein one or both R$_3$ is H and more preferably both R$_3$ are C$_{1-4}$ alkyl e.g. methyl.

In another particular embodiment X is the group

R$_2$—Q---- wherein Q is C(O)NH and R$_2$ is a steroid group. Preferably R$_2$ is lanosterol or more preferably cholesterol attached to Q via the 3-position oxygen thereby forming a carboxamide linkage (—OC(O)NH—) to the ring system.

In a particular embodiment, Y is C$_{1-1}$ alkylene, C$_{2-12}$ alkenylene or C$_{2-12}$ alkynylene optionally substituted with alkyl, amino, aminoalkyl, guanidino, guanidinoalkyl, amidino or amidinoalkyl, and optionally interrupted with —NR$_3$—, —N$^+$(R$_3$)$_2$—, —C(O)—, —NH—C(NH)—, —C(NH)NH— or —NH—C(NH)—NH— wherein R$_3$ is as previously defined and preferably H or methyl. By "interrupted" is meant that a portion of the alkylene, alkenylene or alkynylene chain is linked via one of the specified divalent groups to a remaining portion of the chain, the total number of carbon atoms being preserved. It will be appreciated that the substituents amino, aminoalkyl, guanidino, guanidinoalkyl, amidino and amidinoalkyl as well as interrupting groups —$N^+(R_3)_2$—, —NH—C(NH)— and —NH—C(NH)—NH— at physiological pH incorporate a positively charged nitrogen atom. Preferred substituents include one or more aminoalkyl e.g. aminobutyl, the amino acid side chain for lysine (Lys, K) and guanidinoalkyl e.g. guanidinopropyl, the amino acid side chain for arginine. In a preferred embodiment, Y is $C_{1-6}$ alkylene interrupted by the positively charged divalent group —$N^+(R_3)_2$—. Preferably $R_3$ is $C_{1-4}$ alkyl e.g. methyl. In a preferred embodiment, Y is $C_{1-6}$ alkylene interrupted by the positively charged divalent group —NH—C(NH)— or —C(NH)NH—. In a particularly preferred embodiment, Y is —C(O)NH—(CH$_2$)$_2$—NH—C(NH)—(CH$_2$)$_3$—.

In another particular embodiment, Y is an amino acid residue or a peptidic group selected from:

(II)

(III)

(IV)

(V)

wherein
$R_3$ is H or $C_{1-4}$ alkyl;
$R_4$ is H, OH, N(R$_3$)$_2$, or $C_{1-4}$ alkyl;
$R_5$ is independently an amino acid side chain;
$R_6$ is H, $C_{1-4}$ alkyl or $C_{1-4}$ acyl;

m is an integer from 0 to 30;
n is an integer from 1 to 100;
o is an integer from 1 to 30;
p is an integer from 0 to 100; and
t is an integer 0 or 1.

Groups (II) to (V) are peptidic having length n of 1 to 100 residues and may be a targeting moiety, for example, the peptide codes for a cell surface receptor ligand. Preferably n is 1–50, more preferably 1–10 and most preferably 1 to 5. Preferably the peptide has an overall positive charge at physiological pH i.e. there is at least one $R_5$ group which corresponds to the side chain of amino acids lysine (Lys, K) or arginine (Arg, R). By "amino acid" side chain is meant to include the side chain from any naturally or non-naturally occurring α or β, D or L amino acid. Examples of non-naturally occurring side chains include halo- and cyano-substituted benzyl, tetrahydroisoquinolylmethyl, cyclohexylmethyl, and pyridylmethyl.

The peptidic group of Y may be attached to X on the one hand or the sulfur atom S of the disulfide bond on the other via an alkyl chain of length m or v respectively. Preferably m is 0 to 30 and v is 1 to 30. More preferably m and v are both independently 1 to 10 and even more preferably 1 to 4. An amide linkage to the peptide formed when t=1 may be made resistant to enzymatic degradation when $R_3$ is $C_{1-4}$ alkyl e.g. methyl. In another embodiment $R_3$ is H.

In the case where Y is group (IV) or (V), the peptide incorporates at least 1 cysteine residue, the sulfur atom of which serves as one of the sulfur atoms of the disulfide bond defined in lipid compounds of formula (I). The length of the peptide in these embodiments is the sum total of n and p. In preferred embodiments, the sum of n and p is 0 to 100, more preferably 0 to 50, 0 to 10 and most preferably 0 to 4. Terminal group $R_4$ may be OH as in a natural peptide or may be modified to resist enzymatic degradation when H, alkyl (e.g. methyl) or amino (e.g. NH$_2$). Terminal group $R_6$ may be H as in a naturally occurring peptide or may be modified to resist enzymatic degradation when a group such as acyl e.g. acetyl, or alkyl e.g. methyl.

In a particular embodiment, hydrophilic head portion Z is $C_{1-12}$ alkyl, $C_{2-12}$ alkenyl or $C_{2-12}$ alkynyl substituted with one or more carboxyl or carboxyalkyl group such that at physiological pH Z carries an overall negative charge. Preferably Z includes acetic acid and succinic acid linked to the sulfur atom of the disulfide bond in (I) by a bond to a non-carbonyl carbon atom. Z may also be an oligonucleotide such as an antisense oligonucleotide conjugated to the disulfide sulfur atom by a linker. A suitable linker in this embodiment is an alkylene, alkenylene, or alkynylene chain attached to a functional group on the oligonucleotide. Preferably the linker group is attached to a terminal residue e.g. at one of the 5', 3' or 2' hydroxyl groups or may be attached to a 2' hydroxyl group of a non-terminal residue.

Alternatively, Z may be represented by a group selected from:

(VI)

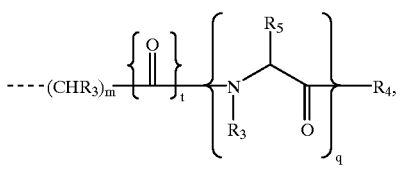

-continued

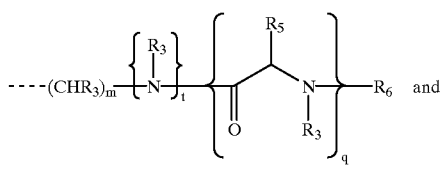

(VII)

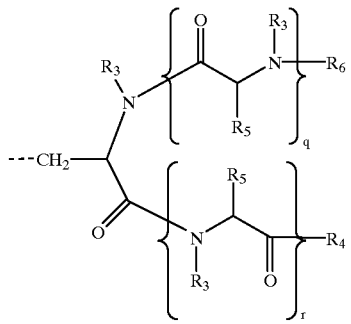

(VIII)

wherein
$R_3$ is H or $C_{1-4}$ alkyl;
$R_4$ is H, OH, $N(R_3)_2$, or $C_{1-4}$ alkyl;
$R_5$ is independently an amino acid side chain;
$R_6$ is H, $C_{1-4}$ alkyl or $C_{1-4}$ acyl;
m is an integer from 1 to 30;
q and r are both independently an integer from 0 to 200 and the sum of q and r is from 0 to 200; and
t is an integer 0 or 1.

Groups (VI) to (VIII) are peptidic having length q (q+r for group VIII) of 1 to 100 residues and may be a targeting moiety, for example, the peptide codes for a cell surface receptor ligand. Preferably q is 1–50, more preferably 1–10 and most preferably 1 to 5. Preferably the peptide has an overall negative charge at physiological pH i.e. there is at least one $R_5$ group which corresponds to the side chain of amino acids aspartate (Asp, D) or glutamate (Glu, E). The peptidic group of Z may be attached to the sulfur atom S of the disulfide bond via an alkyl chain of length m which may form an amide linkage to the peptide when t=1. Preferably m is an integer from 0 to 30, more preferably 1 to 10 and most preferably 1 to 4. Amide bonds in Z may be made resistant to enzymatic degradation when $R_3$ is $C_{1-4}$ alkyl e.g. methyl. In another embodiment $R_3$ is H.

In the case where Z is group (VIII), the peptide incorporates at least 1 cysteine residue, the sulfur atom of which serves as one of the sulfur atoms of the disulfide bond defined in lipid compound of formula (I). The length of the peptide in this embodiment is the sum total of q and r. In preferred embodiments, the sum of q and r is an integer from 0 to 100, more preferably 1 to 50, 1 to 10 and most preferably 1 to 5. In a particular embodiment one of q and r is 0 while the other is 1 to 10. In another particular embodiment, one of q and r is 0 while the other is 1, wherein the sole $R_5$ substituent is an Asp or Glu side chain. Similar to groups (IV) and (V), terminal group $R_4$ of (VIII) may be OH as in a natural peptide or may be modified to resist enzymatic degradation when H, alkyl (e.g. methyl) or amino (e.g. $NH_2$). Terminal group $R_6$ of (VIII) may be OH as in a naturally occurring peptide or may be modified to resist enzymatic degradation when it is a group such as H, acyl (e.g. acetyl), or alkyl (e.g. methyl).

In a particular embodiment, the hydrophilic head portion Z of lipid compounds of the invention incorporate a targeting molecule which serves to direct the lipid compound, and thus liposomes comprising them, to particular cell, tissue or organ types of interest. Targeting molecules may be peptidic such as proteins or peptides or small molecules. Protein targeting molecules include antibodies i.e. mono or polyclonal which selectively bind to antigenic determinants that are predominant at the site of interest. Protein and peptide targeting molecules are preferably those that are selective ligands for cell surface receptors. For example, certain growth factors such as EGF (epidermal growth factor) and PDGF (platelet derived growth factor) are overexpresssed on the surface of certain cancer cells. The proteins EGF and PDGF therefor serve as a suitable targeting molecule for directing liposomes containing anticancer agents. More preferably, targeting molecules are peptide fragments of proteins which bind to cellular receptors. Similarly, certain small organic molecules are ligands for cell surface receptors. For example, folic acid receptors are known to be overexpressed in certain cancer cells. Consequently folate is a useful targeting molecule for delivering anticancer agents to cancer cells. In this particular instance, folate may serve as the negative charge to the distal region of the hydrophilic head portion.

Targeting molecules may be linked to lipid compounds of the invention or other lipids that comprise liposomes of the invention via a linking group attached via a functional group. Suitable linking groups include peptides, hydrocarbon chains such as alkyl, or other polymers. A particularly preferred linking group is polyethylene glycol (PEG) of approximately 1 to 250 repeating units, preferably about 20 to 100 repeating units and more preferably 70 to 80 repeating units.

Particular lipid compounds of the invention include:

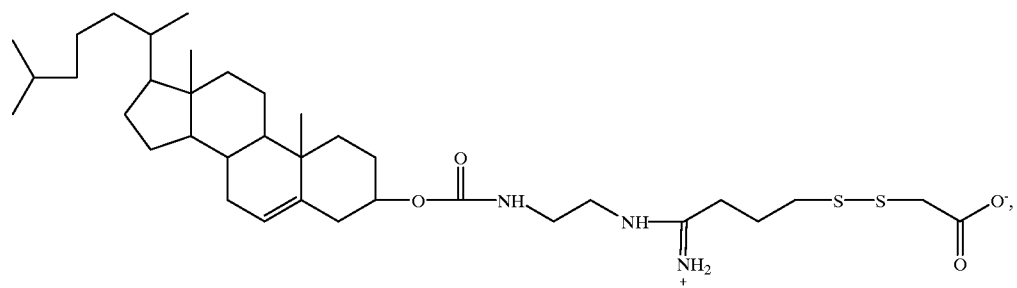

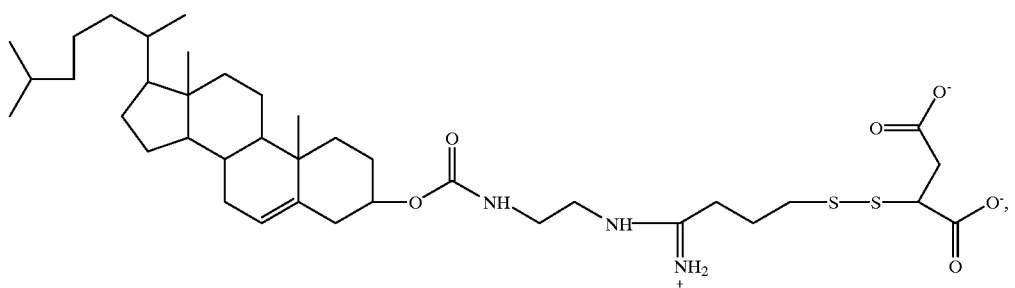
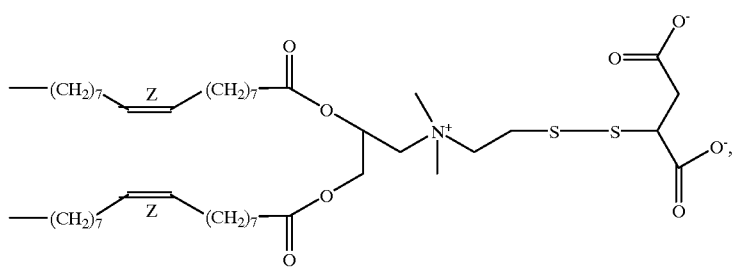
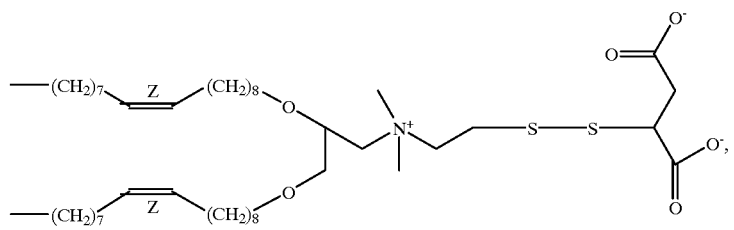
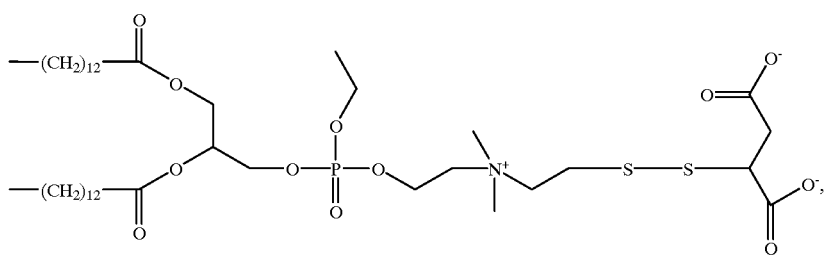
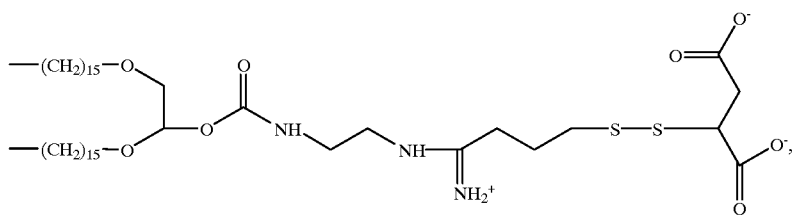

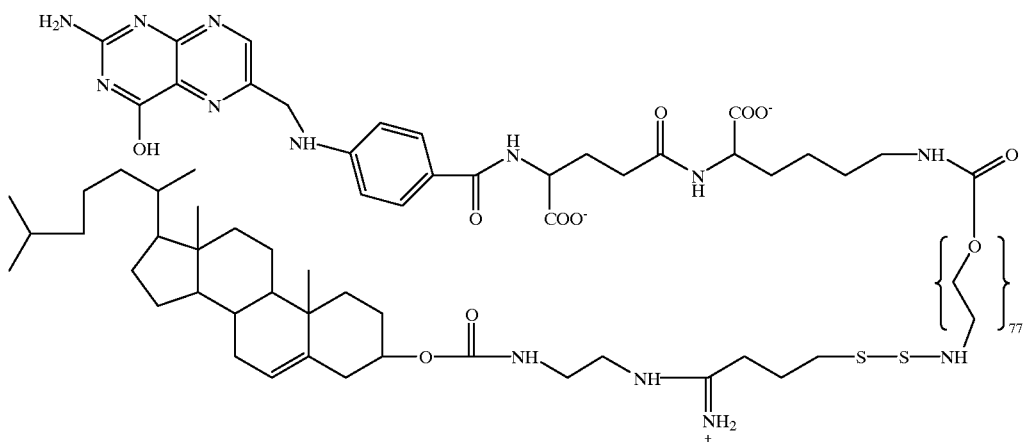

and salts, preferably pharmaceutically acceptable salts, solvates and hydrates thereof. It will be appreciated that compounds of the invention include those compounds defined herein in fully or partially ionized form i.e. salts as well as non-ionized form, each of which being encompassed. Counter ions associated with ionized groups of the compounds are derived from salts, preferably "pharmaceutically acceptable" salts. Suitable counter ions are known to the skilled artisan (see Berge et al, J Pharma Sci (1977) 66:1), and include acetates, salicylates, sulfates, phosphates, arsenates, borates, nitrates, chlorates, metal ions, amines, imidazoles, pyridinium groups, sulfonium groups and phosphonium groups protonated amines, quarternary amines, imidazoles, sulfonium groups, phosphonium groups, pyrroles, tetrazoles. Preferred counter ions include $H^+$, $Na^+$, $K^+$, $Mg^{2+}$, $Ba^{2+}$, $Ca^{2+}$, $Cl^-$ and $Br^-$.

Lipid compounds of the invention are prepared according to established organic chemical synthetic techniques and would be readily apparent to the skilled artisan. In general, compounds may be prepared by the following scheme 1a or 1b or permeations and combinations thereof:

Scheme 1a

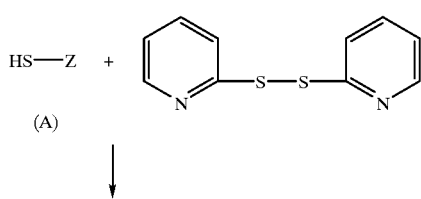

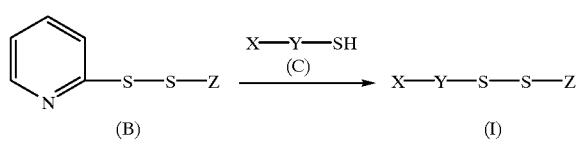

Scheme 1b

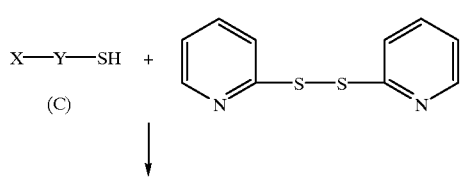

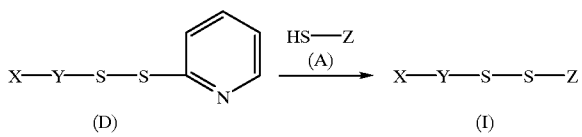

wherein X, Y, and Z are as previously defined. In the two related schemes, intermediate A or C is reacted with 2,2'-dipyridyldisulfide to give pyridylsulfide intermediate B or D respectively which is in turn reacted with sulfhydril intermediate C or A respectively to give final product, compound (I).

In a preferred embodiment, Y incorporates an amidino group which is protonated and therefore cationic under physiological conditions. The following scheme 2 may be employed to synthesize such lipid compounds.

Scheme 2

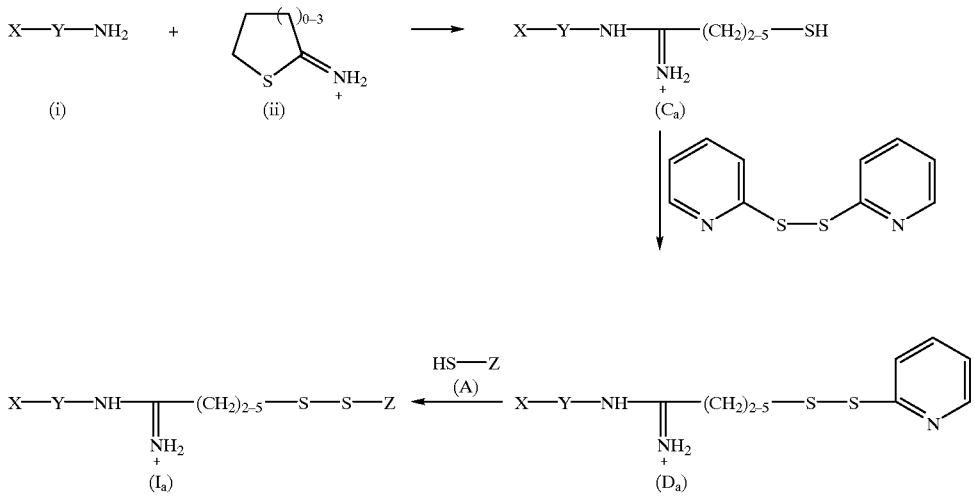

wherein X, Y and Z are as previously defined. Intermediate (i), having a free amino group incorporated in Y, is reacted with a Traut's reagent (ii) to give a thiol-alkyl-amidinium intermediate ($C_a$), which is subsequently reacted with 2,2'-dipyridyldisulfide to give final compound ($I_a$). In particular embodiments, the reagent (ii) is the Traut's reagent wherein the ring is five membered (thienyl) and consequently the terminal thiol group —SH in intermediates ($C_a$), ($D_a$) and the disulfide group in final product ($I_a$) is linked to the amidinium group by a propyl chain. It will be understood that providing unsaturation within and/or substituents e.g. alkyl, on (ii) will provide unsaturation and/or a substituted e.g. branched linking group.

In another preferred embodiment, wherein Y incorporates a quaternary (cationic) amino moiety, and X incorporates a pair of hydrophilic moieties $R_1$, such lipid compounds of the invention may prepared according to schemes 3a or 3b below.

Scheme 3

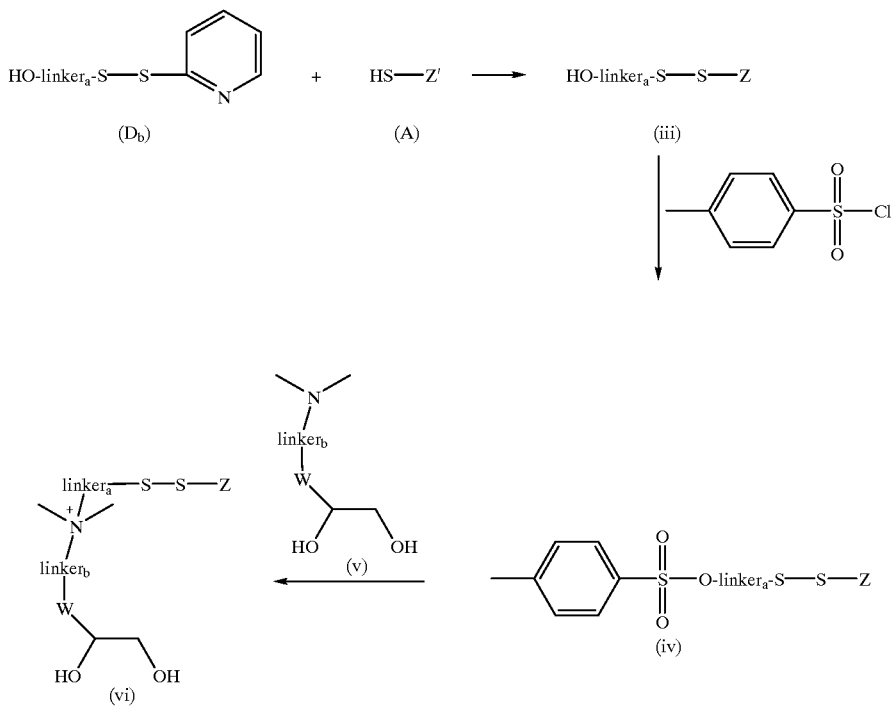

-continued

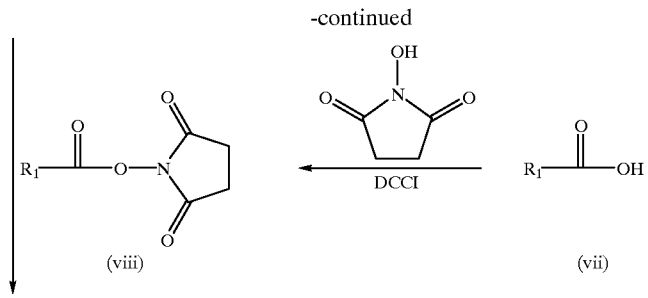

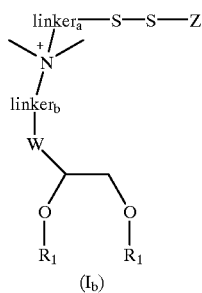

wherein W, Z and $R_1$ are as previously defined and $linker_a$ and $linker_b$ together with the quaternary amine form substituent Y. The 2-pyridylsulfide intermediate ($D_b$), which may be prepared in the same manner as intermediates (D) and ($D_a$) of schemes 1b and 2 respectively, is reacted with thiol (A) to give hydroxyl intermediate (iii). Hydroxyl intermediate (iii) is then reacted with tosyl chloride (TsCl) to give tosylate intermediate (iv) which in turn is reacted with tertiary amine (v). Tertiary amine (v) may be commercially available or may be synthesized according to established organic synthetic techniques from commercially available starting materials. Reacting (iv) and (v) yields quaternary amine (vi) which is reacted with activated fatty ester (viii) to give final product ($I_b$). Fatty ester (viii) is prepared from the corresponding fatty acid reacted with an activating reagent e.g. dicyclohexylcarbodiimide (DCCI), and N-hydroxy succinimide. In particular embodiments Z is chosen from 2-succinate, 2-ethylacetate, a peptide or folate linked to the disulfide group via a tethering group such as polyethylene glycol (PEG), each of which is to have an overall negative charge at physiological pH. In another particular embodiment, $linker_a$ is an alkyl chain e.g. ethylene, $linker_b$ is alkyl or more preferably a bond between W and the quaternary amine, and W is $CH_2$.

In a related embodiment, wherein Y incorporates a quaternary amine and the hydrophobic moiety X comprises a steroid group, such lipid compounds of the invention may be prepared according to scheme 4 below.

Scheme 4

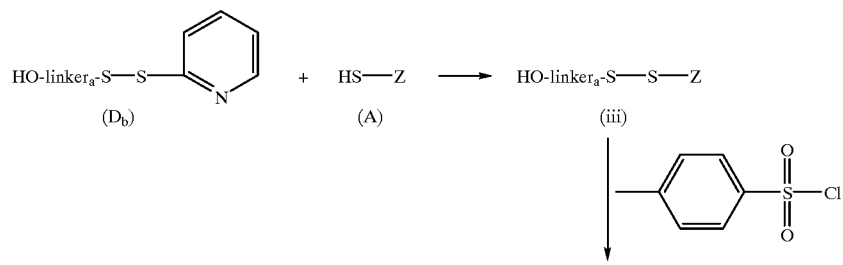

-continued

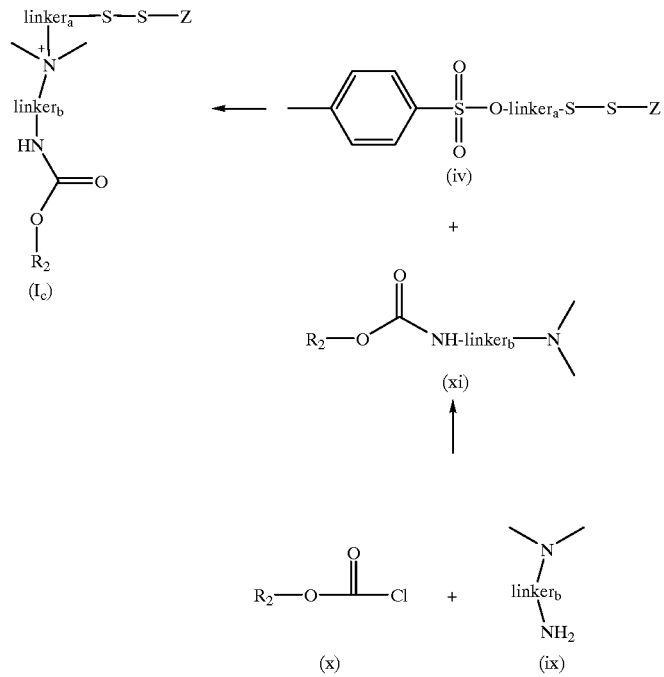

wherein Z, $R_2$, linker$_a$ and linker$_b$ are as previously defined. Hydrophobic moiety (x) is reacted with intermediate (ix) to give intermediate (xi), which is then reacted with s intermediate (iv) to give final product ($I_c$). In a preferred embodiment linker$_a$ and/or linker$_b$ is an alkyl chain e.g. ethylene; $R_2$ is the steroid cholesterol; and Z is as described in the context of scheme 3.

In another embodiment, Z of the lipid compounds of the invention incorporates a folate targeting molecule. These compounds may be prepared according to scheme 5 below.

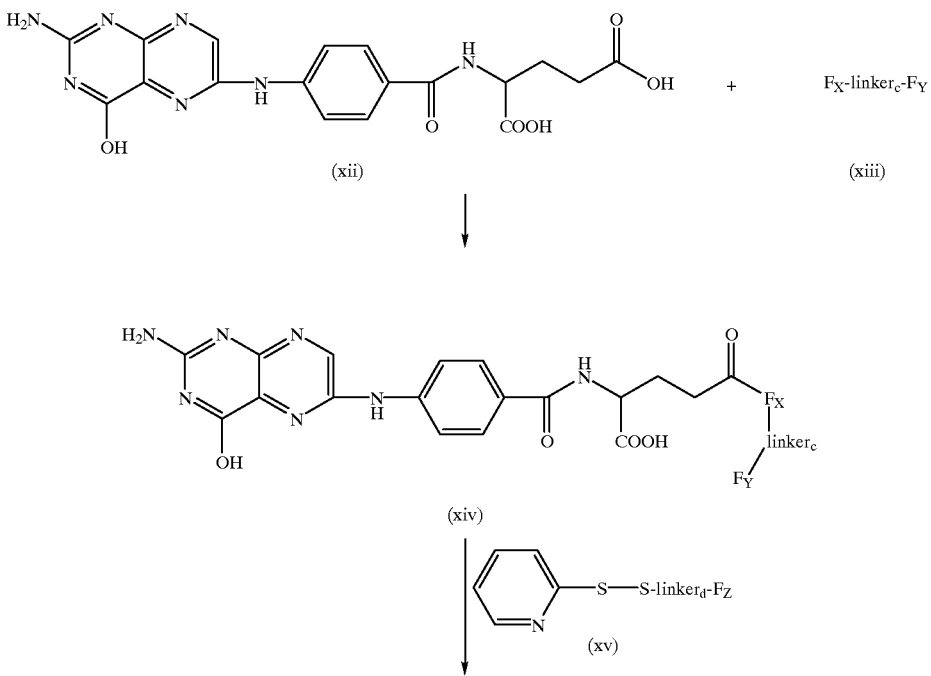

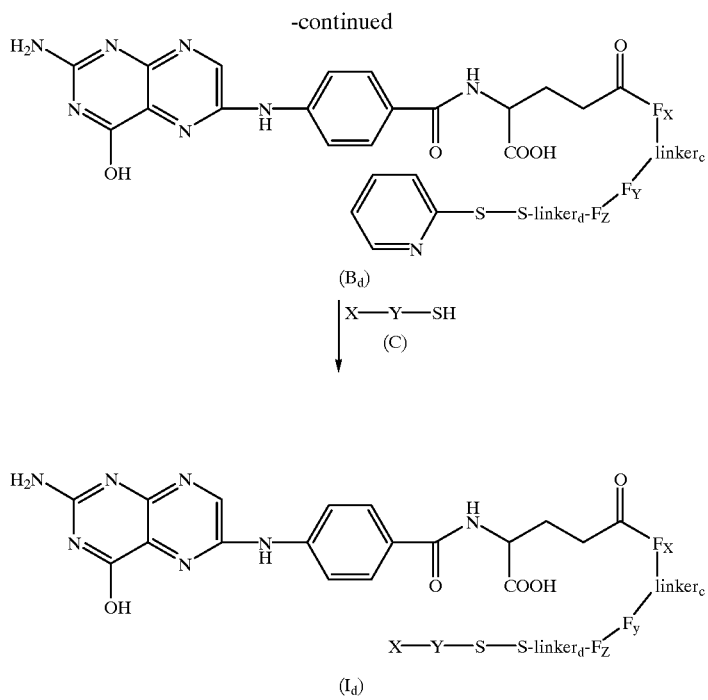

wherein X and Y are as previously defined; $F_x$ is a functional group capable of forming a bond to the carboxyl group of the folate; $linker_c$ is a linking group or spacer connecting $F_x$ to $F_y$ or is a bond; $F_y$ and $F_z$ are functional groups capable of forming a bond with one another; $linker_d$ is a linking group or spacer connecting the disulfide bond from functional group $F_z$.

In a preferred embodiment, $F_x$ in intermediate (xiii) is an amine which forms an amide bond with the carboxyl group of folate which is first converted to an ester or an acid halide e.g. acid chloride. Alternatively $F_x$ is a hydroxyl group which is capable of reacting with the carboxyl of folate or the acid halide derivative thereof. $F_y$ is a functional group capable of forming a bond with $F_y$ which is also a functional group. Preferably one of $F_y$ and $F_z$ is an amino or hydroxyl group while the other is a carboxyl, ester or acid halide. More preferably $F_y$, $linker_c$ and $F_y$ together is an amino acid having a side chain incorporating a functional group e.g. aspartate, glutamate, lysine and cysteine, wherein $F_z$ is the α-amino group, linkers is the α-carbon/α-carboxyl and side chain and $F_y$ is the functional group on the side chain. In a particular embodiment the amino acid is lysine. In another particular embodiment the amino acid is cysteine.

$Linker_d$ is preferably a long chain, stable under physiological conditions such as an alkylene, alkenylene or alkynylene chain optionally interrupted by a heteroatom such as O, S, or N. Preferably $linker_d$ is a polyethylene glycol (PEG) polymer of about 2 to 150 units, more preferably 50 to 100 units, even more preferably 70 to 80 units and most preferably 77 units in length. A terminal hydroxyl group (i.e. $F_y$) of PEG is conveniently used to couple with functional group $F_z$.

It will be appreciated by the skilled artisan that the preceding schemes may require protection and deprotection steps (e.g. amino, hydroxyl, carboxyl, amidino, guanidino) prior to, during or subsequent to the steps defined in any of the preceding schemes. Protecting and deprotecting reagents and procedures are well established techniques in organic chemistry and are explained in detail in Green and Wuts, *Protective Groups in Organic Synthesis*, 2d edition, John Wiley & Sons, New York, 1991.

In another aspect, lipid compounds of the invention are complexed or conjugated to a pharmaceutical agent and in particular with nucleic acid molecules including single or double stranded DNA, RNA or DNA/RNA hybrids.

In another aspect, lipid compounds of the invention are incorporated into unilamelar or multilamellar vesicles, such as micelles or liposomes which are useful for encapsulating pharmaceutical agents therein. Lipid compounds of the invention are generally present in an amount of about 0.1 to about 100 mole percent of the total lipid content depending on the particular compound i.e. depending on the particular hydrophobic tail portion, charge, size. For example about 20 mole percent or less may be appropriate when the lipid compound of the invention has a high molecular weight. In particular embodiments, lipid compounds of the invention are present in liposome compositions in about 30–70 mole percent, the remainder comprising conventional lipids and optionally sterol. In preferred embodiments the am unt of lipid compound of the invention is about 40 to 60 mole percent and more preferably about 50 mole percent.

The remaining lipid content of liposomes of the invention generally comprises one or more vesicle-forming lipids or co-lipids such as those routinely used in liposomes. Such lipids include, for example, those having one, two or more hydrocarbon chains, usually amide, acyl, acyloxy or ether groups, attached to a polar head group, e.g. phospholipids. Suitable phospholipids include phosphatidylcholines such as dilauroyl phosphatidylcholine, dimyristoyl phosphatidylcholine, dipalmitoyl phosphatidylcholine distearoyl phosphatidylcholine, dioleoyl phosphatidylcholine, dilinoleoyl phosphatidylcholine and 1-palmitoyl-2-oleoyl phosphatidylcholine; phosphatidylethanolamines such as 1,2-dioleoyl-3-sn-phosphatidylethanolamine (DOPE), 1,2-distearoyl-3-sn-phosphatidylethanolamine (DSPE) and 1,2-diphytanoyl-3-sn-phosphatidylethanolamine (DiPyPE); and phosphatidic acids such as dimyristoyl phosphatidic acid and dipalmitoyl acid. Preferred phospholipids include phosphatidylethanolamines, in particular dioleoyl phosphatidylethanolamine (DOPE) and diphytanoyl phosphatidylethanolamine (DiPyPE).

Other lipids that can be incorporated into liposomes of the invention include sterols such as cholesterol or ergosterol, glycolipids such as ganglioside $GM_1$ (monosialoganglioside) or hydrogenated phosphatidylinositol, acylglycerol lipids such as 1,2-dipalmitoyl-sn-3-succinylglycerol and sphingolipids such as sphingomyelin. In a particular embodiment, liposomes of the invention may comprise from 2–20 mole percent of a glycolipid and 20–95 mole percent of phospholipid, sphingolipid or mixture thereof. In preferred embodiments, where the liposomes also comprise a sterol or acylglycerol, they may comprise 2–20 mole percent (preferably 4–10) of the glycolipid, 40–80 mole percent (preferably 40–80) of phospholipid, sphingolipid or mixture thereof and 10–50 mole percent (preferably 20–40) of sterol or 5–40 mole percent (preferably 10–30) of acylglycerol.

Liposomes of the invention are prepared according established techniques. For example, the lipid composition is dissolved in an organic solvent, such as an alcohol, ether, halohydrocarbon or mixtures thereof, and the solvent is removed from the resulting solution, for example by rotary evaporation or freeze drying, and the resulting lipid film is hydrated by dispersing in an aqueous medium, such as phosphate-buffered saline or an aqueous solution of a sugar such as lactose, which medium also contains the pharmaceutical agent, to give an aqueous suspension of liposomes in the form of multilamellar vesicles. The aqueous liposome suspension may be treated to reduce the liposome size, for example to give small unilamellar vesicles using established techniques such as sonication or membrane extrusioin e.g. polycarbonate membranes of selected size. Liposomes according to the invention have an average size of below about 1000 nm, and is more preferably in the range of about 50–200 nm and even more preferably 80–120 nm.

Alternatively, lipids of the invention are incorporated in lipid layers of vesicle surrounding a gelatin or solid core. Solid core vesicles may comprises a matrix impregnated with pharmaceutical agents which are subsequently surrounded with a lipid layer. An example of such solid core vesicle are known as "supramolecular biovectors" (SMBVs) which comprise a cross-linked amylose matrix core impregnated with pharmaceutical agents. SMBVs and other similar liposome compositions are described in detail in WO98/29, 557, WO98/29,099, WO98/04,719, WO97/12,618 and WO92/21,330 incorporated herein by reference.

It is generally desirable to have as high a weight ratio of pharmaceutical agent to lipid as possible consistent with liposome stability. The amount of pharmaceutical agent will vary depending on the nature and composition of the agent but in general will be from about 1:10 to about 1:1000.

According to an aspect of the invention, pharmaceutical agents are delivered to an animal, in particular humans, by administering lipid complexes/conjugates or liposomes of the invention to the animal. Administration may be parenteral (intravenous, intraperitoneal, subcutaneous or intramuscular), enteral (oral, rectal, vaginal), topical (dermal), buccal (e.g. sublingual) or by pulmonary inhalation. The dosage form used will depend on mode of administration, the type of therapeutic, prophylactic or diagnostic indication. The dosage amount will also depend on the mode of administration and the indication as well as the individual being treated. The dosage forms of liposomes of the invention include solutions and reconstitutable lyophilized powders, gels, powders or granules, microparticles, nanoparticles, suspensions or solutions in water or non-aqueous media, capsules, sachets, troches, tablets including mini-, micro-and nanotablets, or SECs (soft elastic capsules or "caplets"). Thickeners, flavoring agents, diluents, emulsifiers, dispersing aids, surfactants (e.g. fatty acids such as lauric or capric acid), penetration enhancers (e.g. is bile salts or acids such as UDCA, CDCA), carrier substances or binders may be desirably added to such formulations. The use of such formulations has the effect of delivering to the G.I. tract for exposure to the gastrointestinal mucosa. Accordingly, the formulation can consist of material effective in protecting the nucleic acid from pH extremes of the stomach, or in releasing the nucleic acid over time, to optimize the delivery thereof to the gastrointestinal mucosa. Enteric coatings for acid-resistant tablets, capsules and caplets are known in the art and typically include acetate phtalate, propylene glycol and sorbitan monoleate. Various methods for producing formulations are well known in the art (see *Remington's Pharmaceutical Sciences*, 18th Ed., Gennaro, ed., Mack Publishing Co., Easton, Pa., 1990).

Particular indications of the liposomes will depend on the pharmaceutical agent encapsulated within. Types of pharmaceutical agents which may be encapsulated include small organic molecules, macromolecules and polymers such as peptides, proteins and monoclonal antibodies, nucleic acids such as nucleosides, nucleotides, single stranded oligonucleotides (probes, antisense, ribozymes), double stranded oligonucleotides (plasmids, vectors). In a particular embodiment, oligonucleotides are encapsulated in liposomes of the invention and in particular single stranded oligonucleotides such as those having antisense or ribozyme activity. Oligonucleotides include those incorporating natural structure i.e. 3'–5' phosphodiester linked ribo or deoxyribonucleosides or those incorporating non-naturally occurring features. For example, the backbone of oligonucleotides may be other than phosphodiester such as phosphotriester, phosphorothioate, phosphorodithioate, phosphonates (H, alkyl, aryl), boranophosphate, selenophosphates, ethylene glycol, methylenemethylimino (MMI) and others. Other backbone modifications include 2'–5' is backbone linkages and those having an acyclic sugar-backbone structure such as Peptide Nucleic Acids (PNA's) wherein the sugar and phosphate components are replaced with a peptidic structure.

The sugar component of oligonucleotides may be modified to include hexoses, cyclopentyl or cyclohexyl as well as various substituents at the 21 position including halogen, alkoxy (2'-O-alkyl), alkoxyalkoxy (2'-O-alkyl-alkoxy) and derivatives thereof. Particularly preferred 2' substituents include methoxy, methoxyethoxy (MOE), aminooxyethoxy (AOE) and dimethylaminooxyethoxy (DMAOE), Other non-natural oligonucleotide modfications include base modifications such as 5-methyl-cytosine and 2-aminoadenine and base or sugar functionalization such as cholesterol, intercalators and targetting molecules such as receptor ligands, peptides, antibodies and folic acid. Examples of oligonucleotide that are suitable pharmaceutical agents for encapsulation in liposomes of the invention include:

ISIS-5132  TCCCGCCTGTGACATGCATT (SEQ ID NO:1)

ISIS-2302  GCCCAAGCTGGCATCCGTCA (SEQ ID NO:2)

ISIS-2922  GCGTTTGCTCTTCTTCTTGCG (SEQ ID NO:3)

ISIS-3521  GTTCTCGCTGGTGAGTTTCA (SEQ ID NO:4)

ISIS-2503  TCCGTCATCGCTCCTCAGGG (SEQ ID NO:5)

ISIS-13312 GCGTTTGCTCTTCTTCTTGCG (SEQ ID NO:6)

ISIS-5320  TTGGGGTT (SEQ ID NO:7)

wherein (i) each oligo backbone linkage is a phosphorothioate linkage and (ii) nucleosides in bold type incorporate a 2'-O-methoxyethyl sugar modification, and those underlined incorporate cytosine nucleobases having a 5-methyl substituent.

EXAMPLE 1

Synthesis of Cholesterol-ethylenediamine

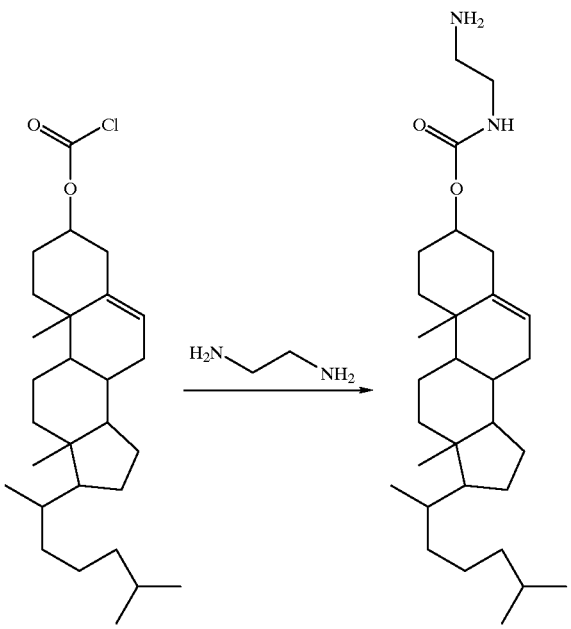

Solid cholesterol chloroformate (10 mmol) was dissolved in 100 mL of dichloromethane (DCM). In a separate flask 0.5 mol ethylenediamine was diluted with 200 mL of DCM and 20 mmol diisopropylethylamine. While stirring, the cholesterol chloroformate solution was drop-wise added to the ethylenediamine solution over a 30 minute period at room temperature (R.T.). Following an overnight R.T. stir, organic solvent was roto-evaporated away using medium vacuum until a minimal sample volume remained. Approximately 400 mL of acetonitrile was added to precipitate the crude product. The solid was then collected by filtration onto a Whatman #5 filter apparatus, rinsed several times with acetonitrile and then air-dried. The crude solid was dissolved in a minimal volume of chloroform and chromatographically purified using a silica column. The purified product presented a single TLC spot (4:1 chloroform/methanol), and a single peak (parent ion M+H=474) was identified by positive mode electrospray.

EXAMPLE 2

Synthesis of Cholesterol-ethylamidinopropyl-pyridyldisulfide

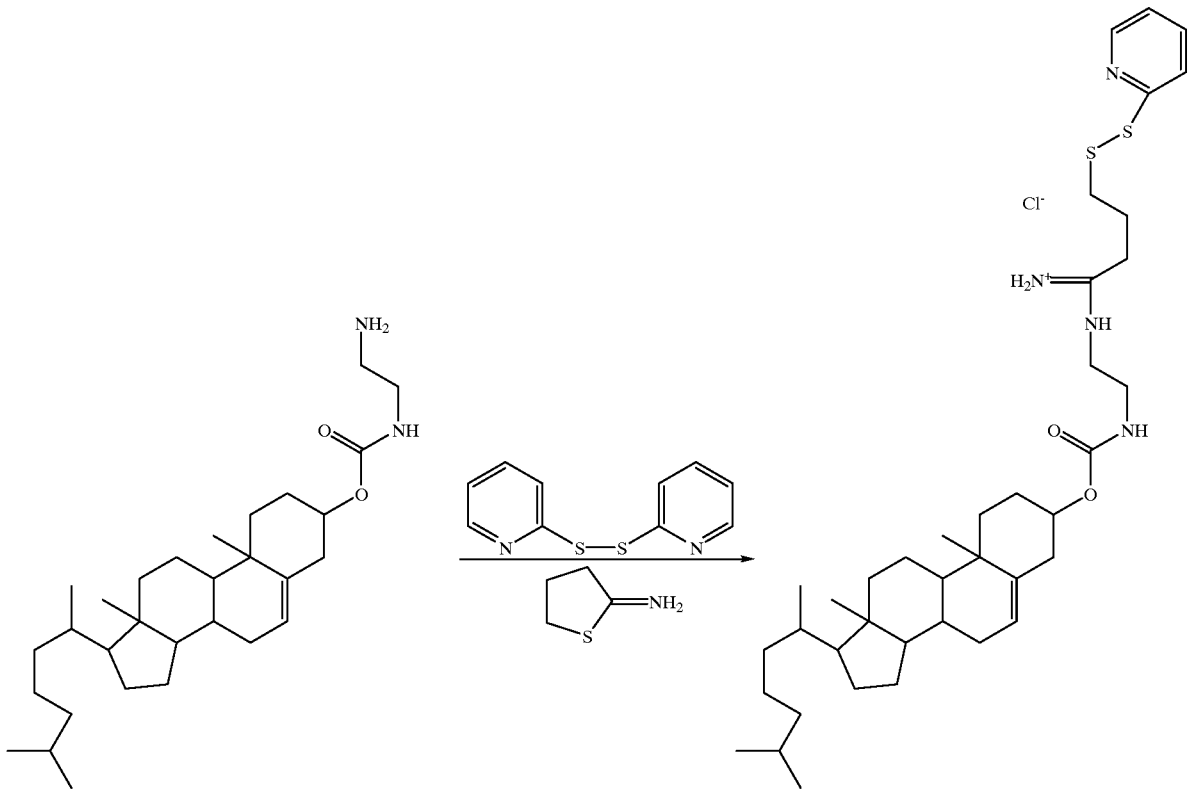

Pure cholesterol-ethylenediamine (10 mmol) was dissolved in 300 mL of DCM. 100 mmol of 2,2'-dipyridyl disulfide was dissolved in 100 mL of methanol and added to the cholesterol-ethylenediamine solution plus 20 mmol of diisopropylethylamine. 15 mmol of 2-iminothiolane was dissolved in 50 mL of methanol and then drop-wise added to the cholesterol-ethylenediamine/2,2'-dipyridyldisulfide solution over 30 minutes at R.T. Following an overnight R.T. stir, organic solvent was roto-evaporated away using medium vacuum until a minimal sample volume remained. Approximately 800 mL of acetonitrile was added to precipitate the crude product. The solid was then collected by filtration onto a Whatman #5 filter apparatus, rinsed several times with acetonitrile and then air-dried. The crude solid was dissolved in a minimal volume of chloroform and chromatographically purified using a silica column. The purified product presented a single TLC spot (4:1 chloroform/methanol), and a single peak (parent ion M+H= 685) was identified by positive mode electrospray.

EXAMPLE 3
Synthesis of CHETA

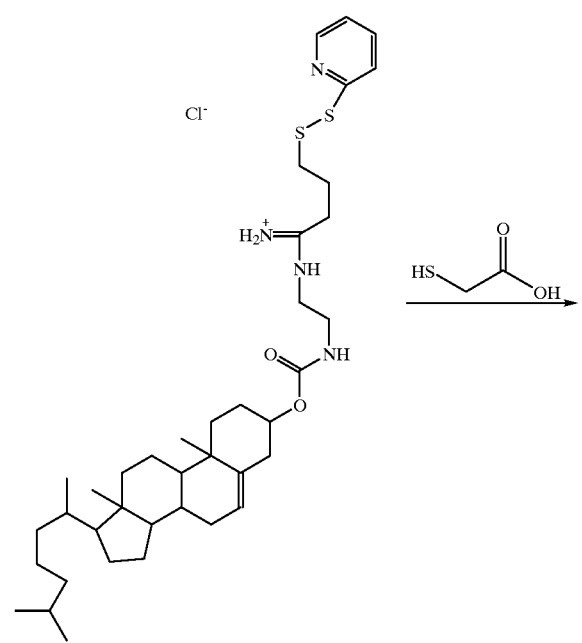

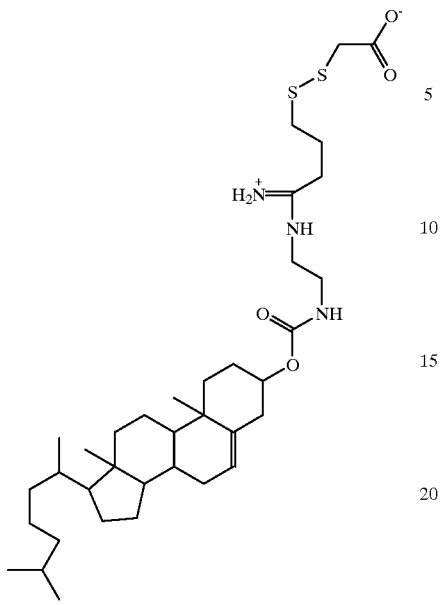

Cholesterol-ethylamidinopropylpyridyl-disulfide is (10 mmol) was dissolved in 200 mL of chloroform. 10 mmol of mercaptoacetic acid was diluted into 20 mL of chloroform plus 50 mmol of diisopropylethylamine. While stirring, the mercaptoacetic acid solution was drop-wise added to the cholesterol-ethylamidinopropylpyridyldisulfide solution over a 1 hour period at R.T followed by an additional 2 h R.T. stir. The organic solvent was roto-evaporated away using medium vacuum until a minimal sample volume remained. Approximately 800 mL of acetonitrile was added to precipitate the crude product. The solid was then collected by filtration onto a Whatman #5 filter apparatus, rinsed several times with acetonitrile and then air-dried. The crude solid was dissolved in a minimal volume of chloroform and chromatographically purified using a silica column. The purified product presented a single TLC spot (4:1 chloroform/methanol), and a single peak (parent ion M+H= 665) was identified by positive mode electrospray.

EXAMPLE 4
Synthesis of CHETSu

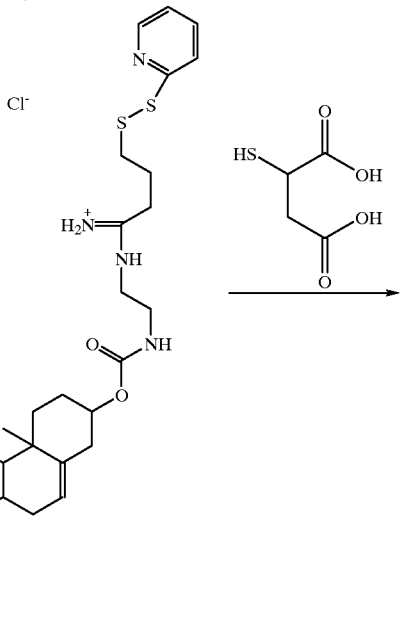

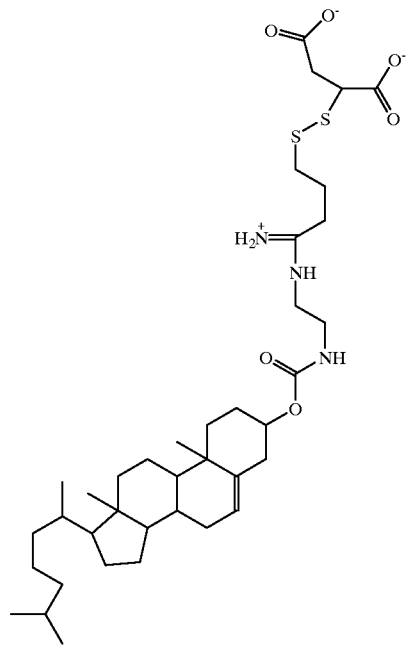

Cholesterol-ethylamidinopropylpyridyl-disulfide (10 mmol) was dissolved in 200 mL of chloroform. 10 mmol of mercaptosuccinic acid was diluted into 20 mL of chloroform plus 50 mmol of diisopropylethylamine. While stirring, the mercaptoacetic acid solution was drop-wise added to the cholesterol-ethylamidinopropylpyridyldisulfide solution over a 1 h period at R.T. followed by an additional 2 h R.T. stir. The organic solvent was roto-evaporated away using medium vacuum until a minimal sample volume remained. Approximately 800 mL of acetonitrile was added to precipitate the crude product. The solid was then collected by filtration onto a Whatman #5 filter apparatus, rinsed several times with acetonitrile and then air-dried. The crude solid was dissolved in a minimal volume of chloroform and chromatographically purified using a silica column. The purified product presented a single TLC spot (4:1 chloroform/methanol), and a single peak (parent ion M−H= 722) was identified by negative mode electrospray.

EXAMPLE 5

Synthesis of CHET-ss-PEG-Folate: 10 mmol Scale

A. Synthesis of cholesteryl-ethylenediamine

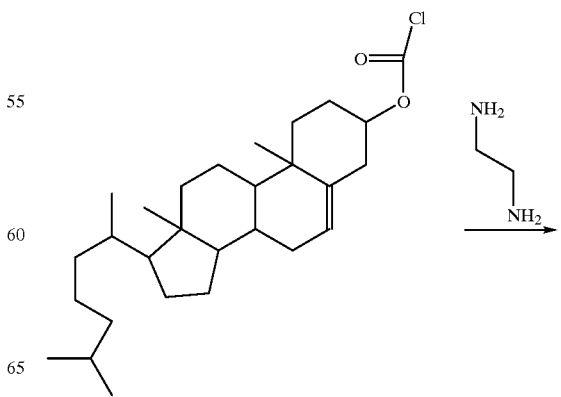

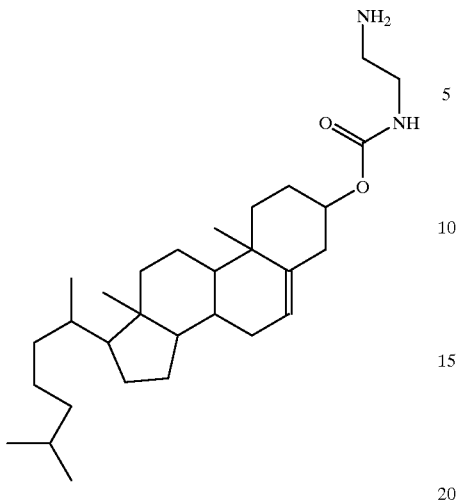

Solid cholesteryl chloroformate (10 mmol) was dissolved in 100 mL of dichloromethane (DCM). In a separate flask 0.5 mol ethylenediamine was diluted with 200 mL of DCM and 20 mmol diisopropylethylamine. While stirring, the cholesteryl chloroformate solution was drop-wise added to the ethylenediamine solution over a 30 minute period at room temperature (R.T.). Following an overnight R.T. stir, organic solvent was roto-evaporated away using medium vacuum until a minimal sample volume remained. Approximately 400 mL of acetonitrile was added to precipitate the crude product. The solid was then collected by filtration onto a Whatman #5 filter apparatus, rinsed several times with acetonitrile and then air-dried. The crude solid was dissolved in a minimal volume of chloroform and chromatographically purified using a silica column. The purified product presented a single TLC spot (4:1 chloroform/methanol), and a single peak (parent ion M+H=474) was identified by positive mode electrospray mass spectroscopy.

B. Synthesis of cholesteryl-ethylenediamine-amidinobutylmercaptan (CHET)

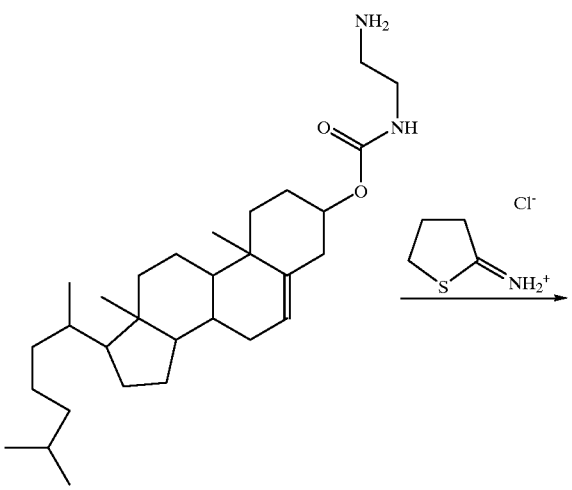

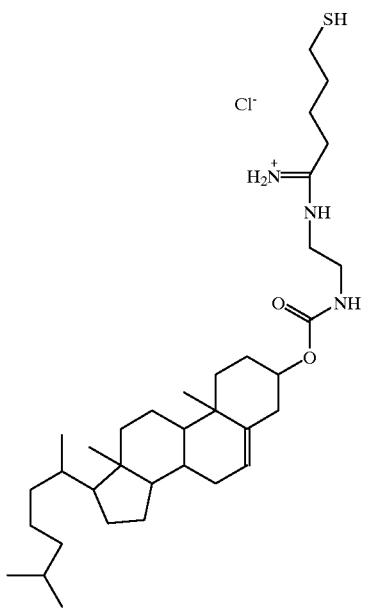

Pure cholesteryl-ethylenediamine (10 mmol) was dissolved in 300 mL of DCM. 15 mmol of 2-iminothiolane (Traut's reagent) was dissolved in 50 mL of methanol plus 20 mmol of diisopropylethylamine. The Traut's solution was then drop-wise added to the cholesteryl-ethylenediamine solution over 30 minutes at R.T. Following an overnight R.T. stir, organic solvent was roto-evaporated away using medium vacuum until a minimal sample volume remained. Approximately 800 mL of acetonitrile was added to precipitate the crude product. The solid was then collected by filtration onto a Whatman #5 filter apparatus, rinsed several times with acetonitrile and then air-dried. The crude solid was dissolved in a minimal volume of chloroform and chromatographically purified using a silica column. The purified product presented a single TLC spot (4:1 chloroform/methanol), and a single peak (parent ion M+H=574) was identified by positive mode electrospray mass spectroscopy.

C. Synthesis of Folate-γ-lysine-polyethyleneglycol-pyridyldisulfide

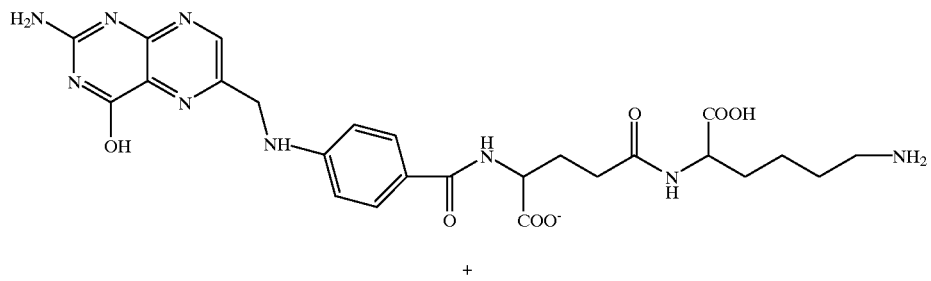

+

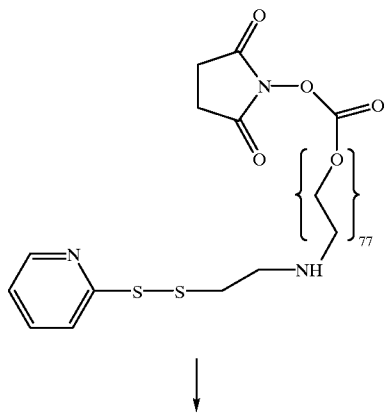

↓

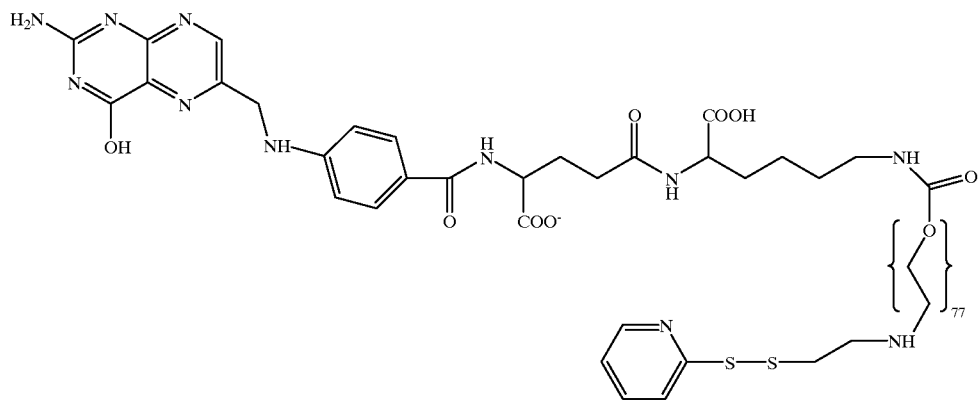

N-hydroxysuccinimidyl-polyethyleneglycol-pyridyldisulfide (10 mmol, synthesized by Shearwater polymers, Huntsville, AL) was dissolved in 500 mL of DMSO plus 0.1 mol triethylamine. 10 mmol of solid folate-γ-lysine (prepared by solid-phase peptide chemistry methodology) was added to the solution while stirring. Following overnight mixing, the solution was added to 20 volumes of ether to precipitate the crude product. The solid was then collected by filtration onto a Whatman #5 filter apparatus, rinsed several times with ether and then air-dried. The crude solid was dissolved in a minimal volume of chloroform containing 2% methanol and then chromatographically purified using a silica column. The purified product presented a single TLC spot (65:25:4 chloroform/methanol/water).

D. Synthesis of CHET-ss-PEG-folate

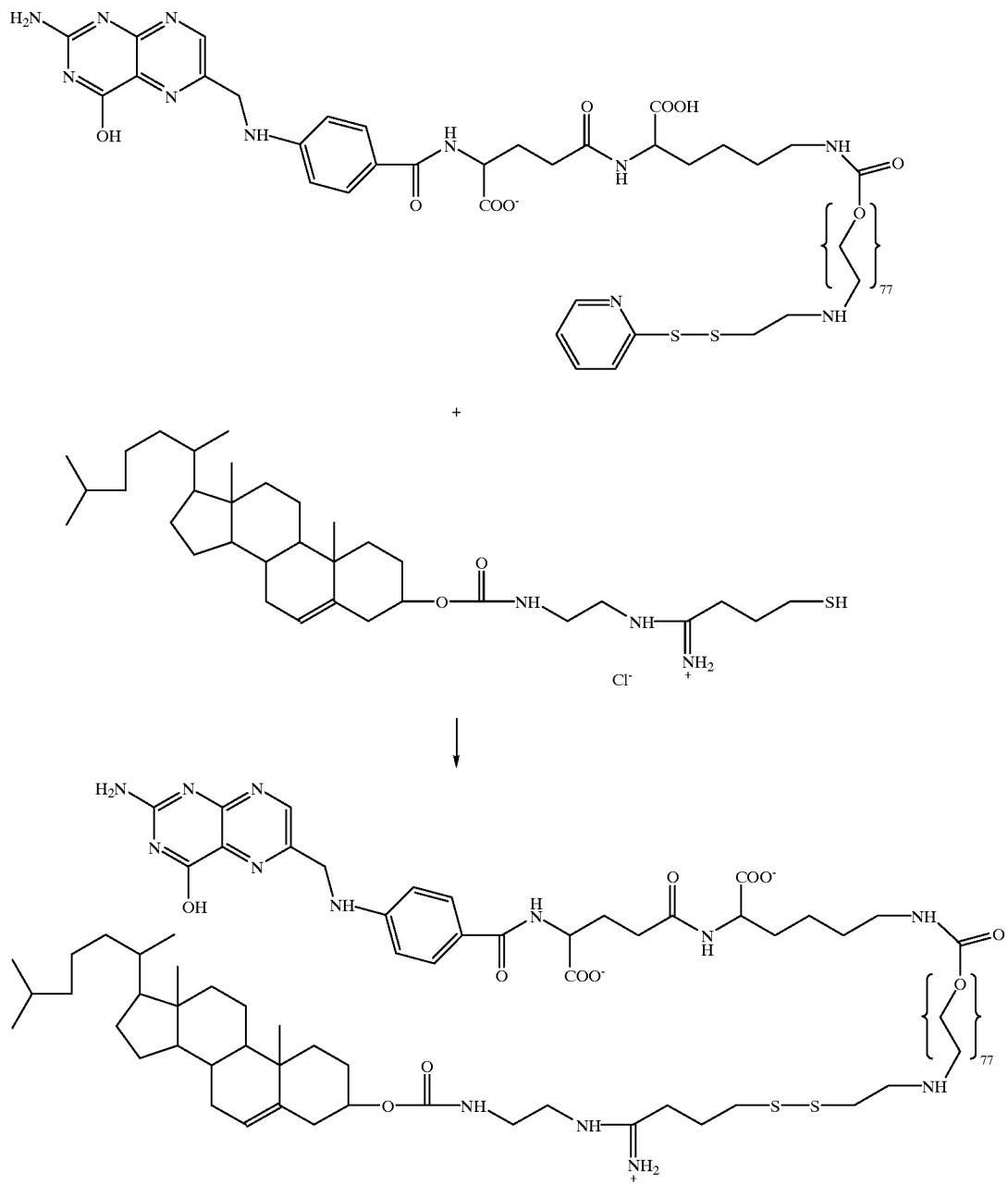

Cholesteryl-ethylenediamine-amidinobutylmercaptan (10 mmol, CHET) was dissolved in 100 mL of chloroform. 10 mmol of folate-γ-lysine-polyethyleneglycol-pyridyldisulfide was diluted into 500 mL of chloroform plus 50 mmol of diisopropylethylamine. While stirring, the folate-γ-lysine-polyethyleneglycol-pyridyldisulfide solution was drop-wise added to the "CHET" solution over a 1 hour period at R.T followed by an additional 2 hour R.T. stir. The organic solvent was roto-evaporated away using medium vacuum until a minimal sample volume remained. The crude product was precipitated with 20 volumes of ether. The solid was then collected by filtration onto a Whatman #5 filter apparatus, rinsed several times with ether and then air-dried. The crude solid was dissolved in a minimal volume of chloroform and chromatographically purified using a silica column. The purified product presented a single TLC spot (65:25:4 chloroform/methanol/water).

EXAMPLE 6

Liposome Preparation

In a 30 mL round bottom flask was added 53.27 mg cholesteryl-{N-[(1-amidinobutyl)aminoethyl]carbamoyl}-dithiosuccinate(CHETSu) and 54.97 mg dioleoylphosphatidyl-ethanolamine (DOPE) in 1 mL chloroform. Chloroform was then evaporated using a rotary evaporator while heating to 60° C. under moderate vacuum until the lipid dried as a thin film on the flask wall. Evaporation was continued under high vacuum for an additional 30 min at 60° C.

A phosphorothioate backbone oligonucleotide ISIS-5132 having the sequence TCCCGCCTGTGACATGCATT (SEQ ID NO:1), targets mRNA transcripts of the C-RAF gene, overexpression of which is associated with cancers. ISIS-5132 was dissolved in water to 100 mg/mL and made isotonic (80–310 mOsm) with the addition of 5 M NaCl. The solution was filtered through a 0.22 μm membrane and 0.5 mL of which was added to the flask containing the lipid film and rotated 240 rpm at 60° C. for 5 min and then vortexed heavily to form large multi-lamellar liposomes. The hydrated mixture was adjusted to pH 7.5 with 0.1 NaOH and then frozen by immersing the flask into a dry ice/acetone bath for 10 min followed by thawing by immersing the flask in 60° C. water bath. The freeze/thaw steps were repeated 5 times giving a creamy solution.

The large multi-lamellar liposomes were converted into near-uniform uni-lamellar liposomes by both i) physical extrusion through polycarbonate membranes (100 nm) and ii) microfluidization. Either technique will produce uni-lamellar liposomes of approximately 90–100 nm in diameter.

Unencapsulated oligonucleotide was separated from the liposomes by gel permeation chromatography (Superdex-200, Pharmacia equilibrated in phosphate-buffered saline, pH 7.4). Liposome fractions were pooled and sterile filtered through a 0.2 μm membrane and stored at 4° C.

EXAMPLE 7

Liposome Fusion Assay

Negatively charged "acceptor" liposomes were prepared comprising egg phosphatidylcholine (eggPC), 1,2-dioleoyl-3-sn-phosphatidylethanolamine (DOPE), 1,2-dipalmitoyl-3-sn-phosphatidylcholine (DPPS) and fluorescent labeled N-(1-pyrenesulfonyl)-1,2-dipalmitoyl-sn-glycero-3-phosphoethanolamine (PS-DHPE) in a molar ratio of 35:50:10:5 respectively. Lipids were hydrated with PBS at pH 7.4 to a total lipid concentration of 1 mM and extruded through 100 nm polycarbonate membrane. Procationic "donor" liposomes, prepared according to the procedures of previous examples, were hydrated with PBS at pH 7.4 to a total lipid concentration of 1 mM as well. In a 15 mL polypropylene test tube 1 mL of pyrene-containing "acceptor" liposome and 1 mL of procationic "donor" liposome was added. Relative fluorescence units ($RFU_{max}$) of the sample was measured using the following parameters: excitation at 343 nm, 5 nm slit width; emission at 483 nm 5 nm slit width; and barrier filter at 430 nm.

While vortexing the test tube, 20 μL of a disulfide reducing agent e.g. 0.5 M dithiothreitol (DTT) stock solution was added. The test tubes were then incubated at 37° C. for 30 minutes and relative fluorescence units ($RFU_{DTT}$) were then measured again. 20 μL of 1% Triton X-100 solution was then added to the test tube to fully quench pyrene's fluorescence and RFU's re-measured ($RFU_{TX}$).

Percent lipid mixing was calculated as ($RFU_{max}$−$RFU_{DTT}$) ($RFU_{max}$−$RFU_{TX}$)×100. In the presence of large excess "donor" liposomes, 60% mixing was the maximum observed. Thus, 60% calculated lipid mixing represents 100% liposome fusion.

For comparison purposes, other disulfide reducing agents were employed in place of DTT including β-mercaptoethanol (BME) and glutathione (GSH) as well as a non-disulfide reducing control, oxidized glutathione dimer glutathione-S-S-glutathione (GSSG).

TABLE 1

% Liposome Fusion* with CHETA liposome

| Time (Sec) | Reducing Reagent | | | | | | | |
|---|---|---|---|---|---|---|---|---|
| | DTT | STD | GSH | STD | BME | STD | GSSG | STD |
| 0 | 0.0 | 0.0 | 0.0 | 0.0 | 0.0 | 0.0 | 0.0 | 0.0 |
| 20 | 50.8 | 4.3 | 2.4 | 1.2 | 3.1 | 4.3 | 0.0 | 0.0 |
| 60 | 83.1 | 2.1 | 5.4 | 3.1 | 62.3 | 1.1 | 0.0 | 0.0 |
| 120 | 90.8 | 2.3 | 13.1 | 3.3 | 71.6 | 3.2 | | |
| 300 | 93.9 | 0.0 | 60.8 | 1.1 | 83.8 | 1.1 | 0.0 | 0.0 |
| 480 | 94.6 | 1.0 | 73.9 | 2.2 | 92.3 | 0.1 | | |
| 600 | 98.4 | 2.3 | 82.5 | 3.5 | 100.0 | 0.0 | 0.0 | 0.0 |

*average % fusion with 5 mM reducing reagent
STD = standard error

EXAMPLE 8

Northern Blot Analysis of Inhibition of c-RAF mRNA Expression

KB Cells obtained from American Type Culture Collection (Rockville, Md.) were grown continuously as a monolayer using RPMI 1640 media containing 10% heat-inactivated fetal calf serum and 2 mM L-glutamine. Cells were seeded on 100 mm plates and treated with oligonucleotide formulations after reaching 70% confluency. Plates were rinsed with 10 mL of pre-warmed PBS, pH 7.4 and 5 mL of serum-supplemented RPMI 1640 was added per plate followed by a small aliquot of oligonucleotide or liposome/oligonucleotide formulation. Following a 2 hr 37° C. incubation, cells were rinsed 3×5 mL with serum-supplemented media and then incubated overnight in a 10 mL volume of serum-supplemented media. Cells were harvested and RNA isolated using standard CsCl purification methodology (Kingston, R. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY. Total RNA was isolated by centrifugation of cell lysates over a CsCl cushion. RNA samples were electrophoresed through 1.2% agarose-formaldehyde gels and transferred to hybridization membranes by capillary diffusion over a 12–14 hour period. The RNA was cross-linked to the membrane by exposure to UV light in a Stratalinker (Stratagene, La Jolla, Calif.) and hybridized to random-primed $^{32}$P-labeled c-RAF cDNA probe (obtained from ATCC) or G3PDH probe as a control. RNA was quantitated using a Phosphorimager (Molecular Dynamics, Sunnyvale, Calif.).

TABLE 2

| Formulation | % C-RAF mRNA | STD* |
|---|---|---|
| ISIS 5132/saline | 95.4 | 3.4 |
| PC/Chol/DSPE-PEG (5132) | 107 | 2.6 |
| PC/Chol/DSPE-PEG-Folate (5132) | 99.4 | 0.45 |
| CHETA/DOPE/DSPE-PEG-Folate (5132) | 69 | 4.5 |

*standard error

What is claimed is:

1. A lipid compound and salts and hydrates thereof having the formula (I):

X—Y—S—S—Z     (I)

wherein:

X is $R_2$-Q;

Q is —(C=O);

$R_2$ is cholesterol;

Y is —NH—$(CH_2)_2$—NH—C(=$N^+H_2$)—$(CH_2)_3$—;

Z is —CH(COO—)($CH_2$COO—);

provided that at a physiological pH, X and Y together have a net positive charge and Z has a net negative charge.

* * * * *

UNITED STATES PATENT AND TRADEMARK OFFICE
CERTIFICATE OF CORRECTION

PATENT NO.   : 6,379,698 B1                                              Page 1 of 1
DATED        : April 30, 2002
INVENTOR(S)  : Leamon et al.

It is certified that error appears in the above-identified patent and that said Letters Patent is hereby corrected as shown below:

Column 19,
Line 55, please delete "$F_2$" and insert therefor -- $F_x$ --;

Signed and Sealed this

Eighth Day of July, 2003

JAMES E. ROGAN
*Director of the United States Patent and Trademark Office*